United States Patent
Krass et al.

(10) Patent No.: US 10,730,210 B2
(45) Date of Patent: Aug. 4, 2020

(54) FLEXIBILITY-CONTROLLED COMPOSITE MATERIAL AND METHOD OF MANUFACTURE

(71) Applicant: Apple Inc., Cupertino, CA (US)

(72) Inventors: Derek C. Krass, Cupertino, CA (US); Douglas J. Weber, San Francisco, CA (US); Jen-Chun Hsu, Taipei (TW); Osamu Yabe, Cupertino, CA (US)

(73) Assignee: APPLE INC., Cupertino, CA (US)

( * ) Notice: Subject to any disclaimer, the term of this patent is extended or adjusted under 35 U.S.C. 154(b) by 259 days.

(21) Appl. No.: 15/032,696

(22) PCT Filed: Oct. 31, 2013

(86) PCT No.: PCT/US2013/067883
§ 371 (c)(1),
(2) Date: Apr. 28, 2016

(87) PCT Pub. No.: WO2015/065460
PCT Pub. Date: May 7, 2015

(65) Prior Publication Data
US 2016/0250782 A1    Sep. 1, 2016

(51) Int. Cl.
*B29C 43/18* (2006.01)
*B29C 70/46* (2006.01)
(Continued)

(52) U.S. Cl.
CPC .............. *B29C 43/184* (2013.01); *A44C 5/00* (2013.01); *A44C 5/0053* (2013.01);
(Continued)

(58) Field of Classification Search
CPC ........ B29C 2043/181; B29C 2043/182; B29C 66/729; B29C 66/72941; B32B 25/10;
(Continued)

(56) References Cited

U.S. PATENT DOCUMENTS 3,570,573 A * 3/1971 Marker ................. B60C 9/0042
152/458
3,802,478 A * 4/1974 Boustany ................ B60C 1/00
152/527
(Continued)

FOREIGN PATENT DOCUMENTS

DE    102010026620    1/2012
EP    1067065         1/2001
(Continued)

*Primary Examiner* — Scott R. Walshon
*Assistant Examiner* — Jasper Saberi
(74) *Attorney, Agent, or Firm* — Morgan, Lewis & Bockius LLP

(57) ABSTRACT

Systems and methods of providing a composite material that is bendable but substantially resists stretching under tension. One embodiment may take the form of a composite material formed by over-molding a woven glass fiber with silicone. The woven glass fiber may be rolled out with a silicon polymer melted into the woven fabric as the rolling process continues. The composite of the two materials may provide a material that bends easily but does not substantially stretch.

15 Claims, 12 Drawing Sheets

(51) Int. Cl.
*B32B 25/10* (2006.01)
*B32B 5/04* (2006.01)
*A44C 5/00* (2006.01)
*A61B 5/00* (2006.01)
*B29C 35/02* (2006.01)
*B29C 43/08* (2006.01)
*B29C 65/00* (2006.01)
*B29K 283/00* (2006.01)
*B32B 3/26* (2006.01)
*B29K 83/00* (2006.01)
*B29K 105/08* (2006.01)
*B29K 309/08* (2006.01)

(52) U.S. Cl.
CPC ............ *A44C 5/0069* (2013.01); *A61B 5/681* (2013.01); *A61B 5/6824* (2013.01); *B29C 35/02* (2013.01); *B29C 43/08* (2013.01); *B29C 66/729* (2013.01); *B29C 70/46* (2013.01); *B32B 5/04* (2013.01); *B32B 25/10* (2013.01); *B29K 2083/00* (2013.01); *B29K 2105/0845* (2013.01); *B29K 2283/005* (2013.01); *B29K 2309/08* (2013.01); *B29K 2995/0082* (2013.01); *B32B 3/266* (2013.01); *B32B 2260/021* (2013.01); *B32B 2260/023* (2013.01); *B32B 2260/046* (2013.01); *B32B 2260/048* (2013.01); *B32B 2307/51* (2013.01); *B32B 2383/00* (2013.01)

(58) Field of Classification Search
CPC ... B32B 25/20; B32B 17/04; B32B 2260/021; B32B 2260/048; B32B 2307/51; B32B 2307/546; B32B 2383/00; B32B 2571/02; B32B 2260/046; B29K 2083/00; B29K 2105/0845; B29K 2083/005; G04B 37/1486; G04B 47/063; A44C 5/14; A44C 5/0053; A44C 5/00; A44C 5/0069; A61B 5/681
See application file for complete search history.

(56) References Cited

U.S. PATENT DOCUMENTS

| | | | | |
|---|---|---|---|---|
| 4,110,139 A * | 8/1978 | Mashida | ............. | A44C 5/0053 156/209 |
| 5,206,079 A * | 4/1993 | Sanada | .................. | B29C 33/62 428/316.6 |
| 5,702,798 A * | 12/1997 | Sugita | .................... | A41D 31/02 428/131 |
| 6,071,834 A * | 6/2000 | Martz | ................ | A41D 31/0016 156/178 |
| 6,234,668 B1* | 5/2001 | Cooper | ............. | G04B 37/1406 224/164 |
| 2003/0157343 A1 | 8/2003 | Yeung | | |
| 2004/0219851 A1* | 11/2004 | Sahlin | ...................... | B32B 5/08 442/254 |
| 2005/0287893 A1* | 12/2005 | Lee | ........................ | B65G 15/34 442/104 |
| 2006/0035550 A1* | 2/2006 | Aseere | ..................... | B32B 3/10 442/180 |
| 2008/0035454 A1* | 2/2008 | Hawkins | ............... | B29C 66/433 198/844.1 |
| 2011/0051569 A1* | 3/2011 | Kitahara | ............... | B29C 70/70 368/282 |
| 2012/0087216 A1* | 4/2012 | Keung | ................ | A44C 5/0084 368/282 |
| 2012/0128928 A1* | 5/2012 | Roberts, III | ............. | B32B 3/08 428/138 |

FOREIGN PATENT DOCUMENTS

EP 1661682 5/2006
GB 2323576 9/1998

* cited by examiner

FIG. 3A
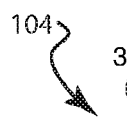
FIG. 3B
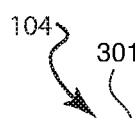
FIG. 3C
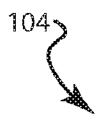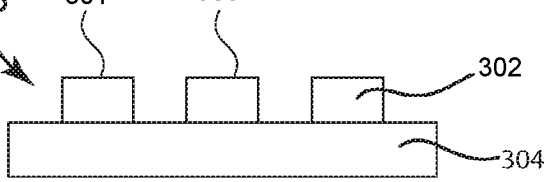
FIG. 3D
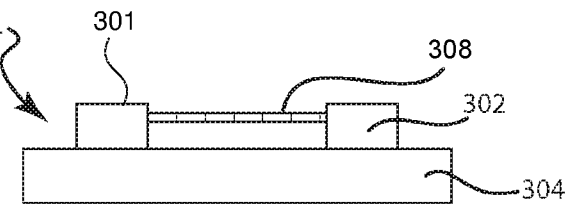
FIG. 3E

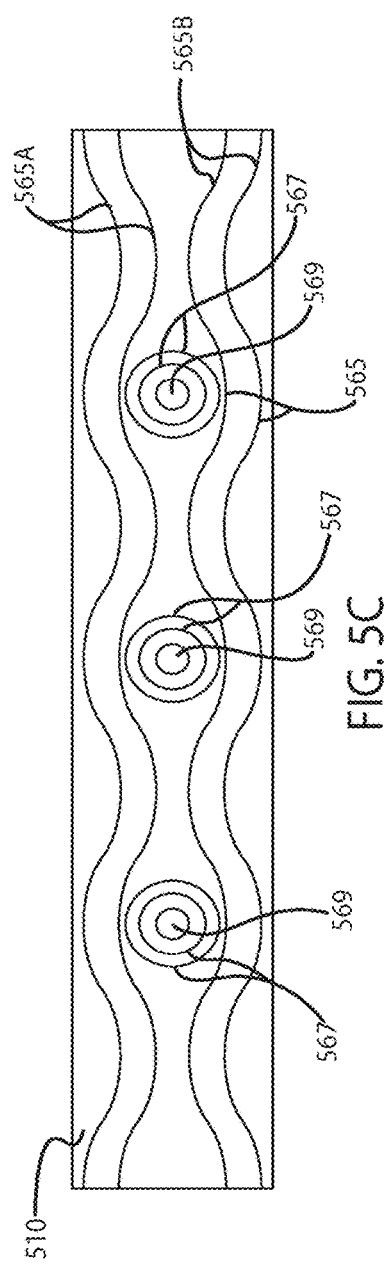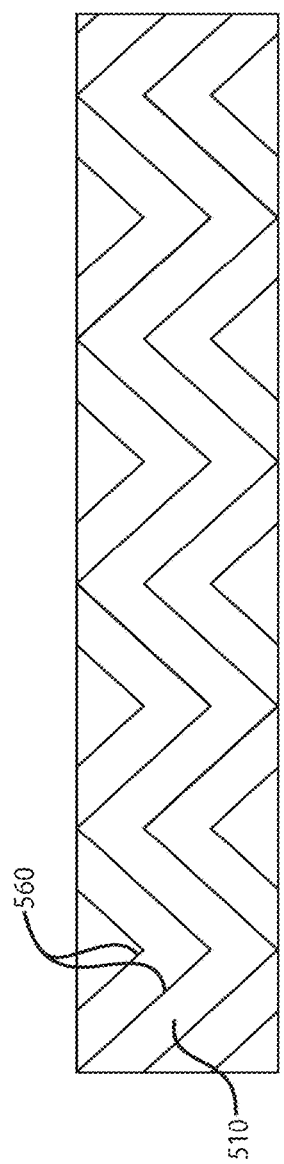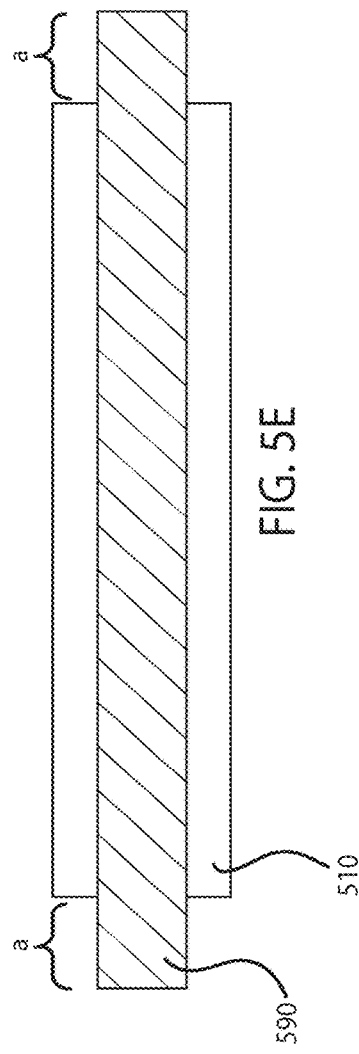

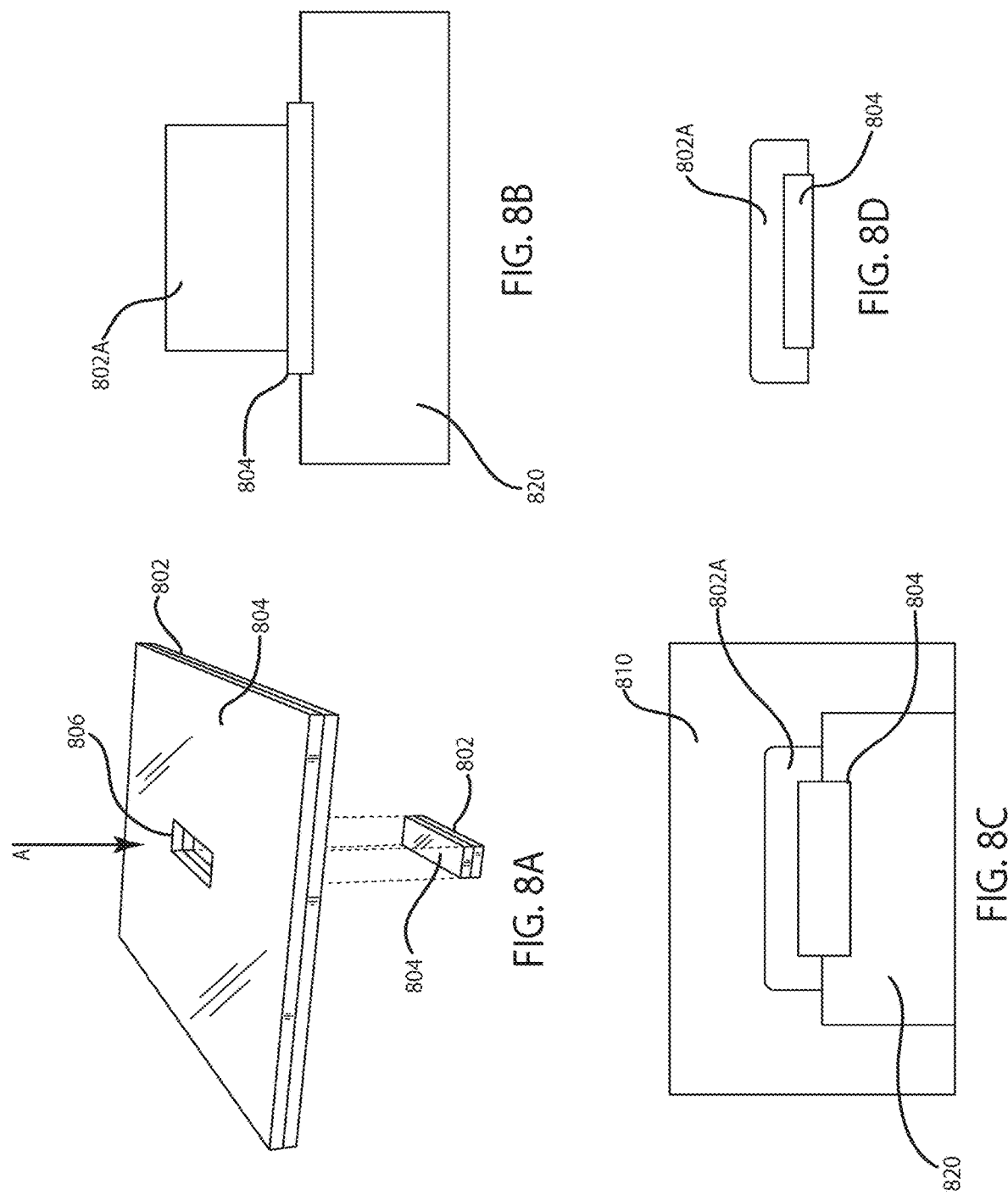

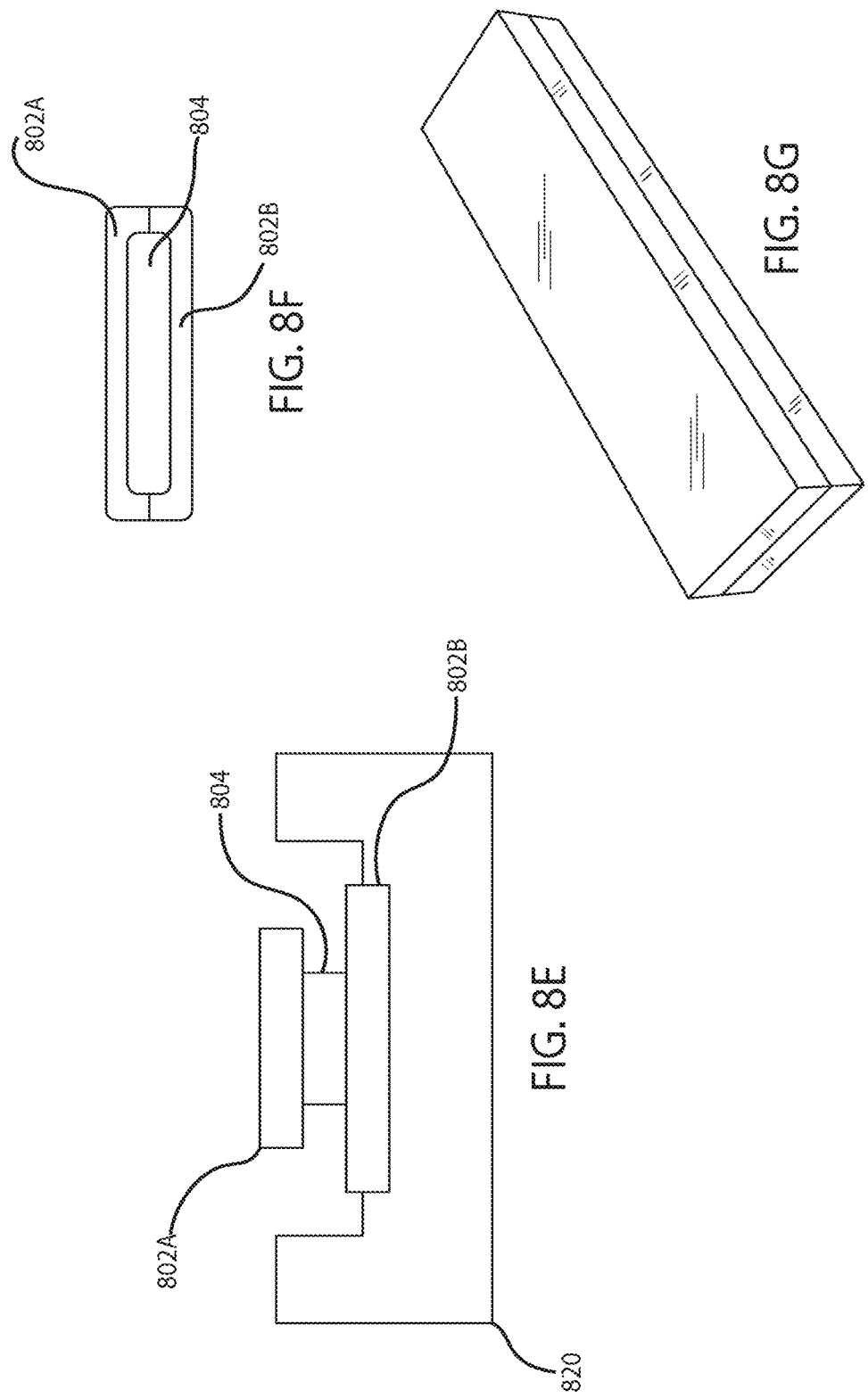

FLEXIBILITY-CONTROLLED COMPOSITE MATERIAL AND METHOD OF MANUFACTURE

CROSS-REFERENCE TO RELATED APPLICATION

This application is a 35 U.S.C. § 371 application of PCT Patent Application No. PCT/US2013/067883, filed Oct. 31, 2013 and titled "Flexibility-Controlled Composite Material and Method of Manufacture," the disclosure of which is hereby incorporated herein by reference in its entirety.

TECHNICAL FIELD

The various embodiments as discussed herein generally relate to flexible materials combined with secondary materials in order to control the overall flexibility of the final material, and more particularly to a flexibility controlled silicone material.

BACKGROUND

Silicone rubber is a synthetic elastomer that possesses excellent mechanical properties such as high tear strength, water and weather resistance. Silicone rubber also has a rubbery consistency which provides a smooth and comforting feel on contact with skin. Silicones are inert, synthetic compounds with a variety of forms and uses. Typically they are heat-resistant and rubber-like, having good elasticity low thermal conductivity, low chemical reactivity, low toxicity, and good thermal stability (with consistent properties between −100 to 250° C.). Silicone rubbers are used in medical applications, cookware, apparel, device covers, and insulation. Silicone rubbers have the ability to repel water and form watertight seals, although silicones are not hydrophobes. Silicones do not support microbiological growth. Silicones are resistant to oxygen, ozone, and ultraviolet (UV) light. These resistances have led to widespread use of silicones in the construction industry (e.g. coatings, fire protection, glazing seals) and the automotive industry (external gaskets, external trim). Silicones also possess electrical insulation properties.

While silicone rubbers may have a variety of practical uses, they still may have a substantial drawback to their natural flexibility. The inherent flexibility of silicone is not necessarily desirable in all applications, especially in applications where flexibilty along a particular axis or direction may be undesirable. As such, modifying the natural flexibility of a silicone rubber product may provide improved utility in a variety of silicone rubber products.

SUMMARY

In accordance with various embodiments, a material such as silicone rubber may be utilized in various consumer products. The various characteristics of silicone rubber may be improved by the inclusion of a second material. Such improvements may be directed at modifying certain flexibility characteristics of silicone rubber while preserving other flexibility characteristics of the silicone rubber. For example, the second material may be applied as fiber strands or woven fabric. The second material may be encapsulated within the silicone rubber. By combining the two materials, the resulting composite material may possess characteristics of all the constituent materials. As such, the flexibility of the silicone rubber in elongation may be decreased reflecting the elongation characteristics of the second material, while another characteristic such as the drape-ability of silicone rubber may be preserved.

One embodiment described herein may take the form of a composite material comprising: a first flexible, bendable, elongatable material; and a second flexible material that resists elongation in at least one direction; wherein the second material is encapsulated by the first material.

Another embodiment described herein takes the form of a composite material, comprising: a first flexible, bendable material that elongates under force; a second flexible, bendable material that resists elongation under force; wherein the second material is embedded in the first material; and the second material comprises a woven fiber fabric.

Still another embodiment takes the form of a method of manufacturing a composite material, the method comprising the operations of: positioning a first layer formed of a flexible material with respect to a second layer formed of a material resisting elongation; positioning a third layer formed of the flexible material adjacent to the second layer; applying heat and pressure to the first, second and third layers, thereby heating and pressing the first and third layers into the second layer to form the composite material.

In accordance with further embodiments, a composite material may include a first material that is flexible in bending and elongation and a second material that is a structured fabric. The second material may be substantially flexible in bending but resists elongation. The second material may be encapsulated within in the first material. The structured fabric may be formed of woven or layered fiber strands. The fibers may be oriented in a first direction and a second direction allowing for control of the elongation and/or the drape of the composite material.

It is to be understood that both the foregoing general description and the following detailed description are for purposes of example and explanation and do not necessarily limit the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

FIG. 3A-E illustrates a cross section side view of various examples of a core structures that may be located within a composite material as viewed across the width of the composite material from view AA indicated FIG. 2A.

FIG. 5A-E illustrates various examples of fabric or fibrous strands laid out along the length of a composite material as viewed as a cross section along the length of the composite material from view BB indicated in FIG. 2A.

FIG. 8A-G illustrates an example of a compression molding process for forming a composite material.

DETAILED DESCRIPTION

Figure 1:
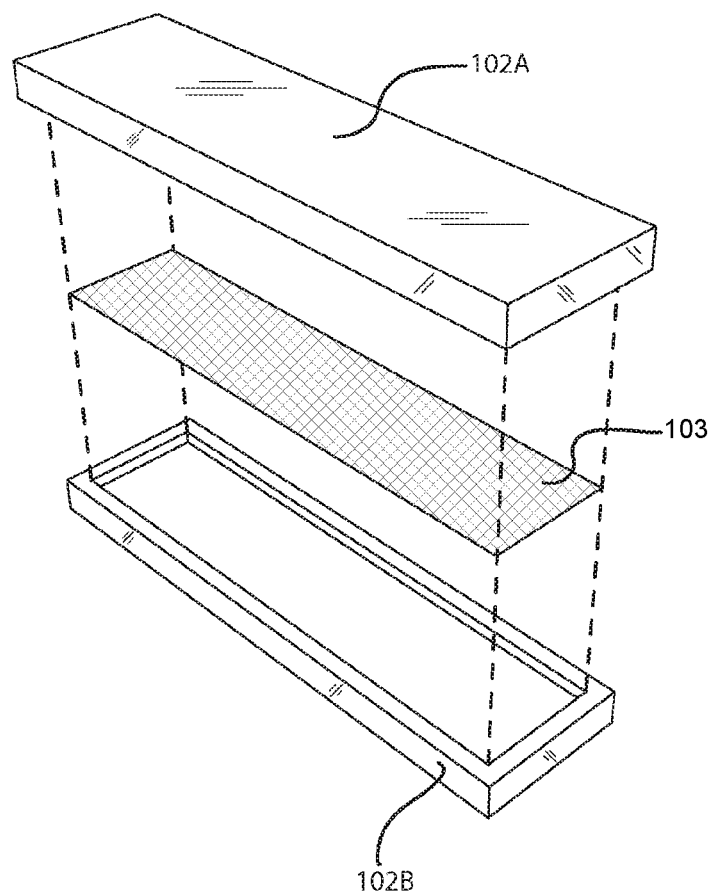
FIG. 1 illustrates a parallel projection view of an exploded example of a composite material.

In accordance with various embodiments, a material such as silicone rubber may be utilized in various consumer products. The various characteristics of silicone rubber may be improved by the inclusion of a second material. Such improvements may be directed at modifying certain flexibility characteristics of silicone rubber (e.g. its natural tendency to elongate in a direction when under force) while preserving other flexibility characteristics (e.g. its natural tendency to drape around a surface that it is applied to) of the silicone rubber. For example, the second material may be fiber strands or woven fabric encapsulated within the silicone rubber. By combining the two materials, the resulting composite material may possess characteristics of all the constituent materials. As such, as an example, the flexibility of the silicone rubber in elongation may be decreased and thus reflect the elongation characteristics of the second material, while another characteristic such as the drapeability of silicone rubber may be preserved.

Various aspects of the second material may be controlled or tuned to provide the second material with the specific characteristics desired. In accordance with various embodiments, the second material may form a core within the first material. The structure of the core may be modified to change the characteristics of the composite material. By modifying the shape of the core (made up of the second material) within the first material, characteristics such as strength, failure points, drape, and/or elongation may be finely tuned. In accordance with various embodiments, the layout or the bias of the second material may also be modified in order to control for specific characteristics. For example, fibers that make up the second material may be laid out in a specific direction. For example, the fabric that makes up the second material may be cut along a certain bias. Additionally, the location, continuity, size, and orientation of the constituents of the second material may be modified in order to control specific characteristics of the composite material.

By controlling the characteristics of the composite material, the composite material may be utilized in improving the functionality of various devices or accessories. For example, the composite material may be utilized in forming device covers, lanyards, straps, bracelets, bands, belts, harnesses or similar components.

In accordance with various embodiments, a composite material may include a first material and a second material. The first material may be a flexible material. Stated another way the first material may be flexible in elongation, flexible across the width, and/or easily bendable. One example of a first material may be silicone. While silicone may be used as the example material throughout this description, it may be noted that other materials may also be utilized as the first material in the composite material. In accordance with various embodiments, the first material or the flexible material may be any material that may be bonded with a second material. Also the first material may be a comfortable material in contact with skin. For example, the first material may include silicone rubber, rubber, nylon, or any other flexible material. The first material may be referred to herein as a "flexible material" or "outer material."

In accordance with various embodiments, the second material may be a resistive material with respect to elongation and a flexible material in bending. The second material may be a material suitable to be used as a fiber. The second material may be a material that may be woven into a fabric of material. The second material may be encapsulated with the first material. For example, the second material may include woven or non-woven glass fiber, carbon fiber, cotton fiber, nylon fiber, KEVLAR fiber (i.e. poly-paraphenylene terephthalamide), TEFLON fiber, or any other similar material. The second material may be referred to herein as a "core," "core material," or "non-stretchable material."

In accordance with various embodiments, as illustrated in FIG. 1, a composite material may include first material 102 and second material 103. It may be noted that the first material 102 and the second material 103 may be combined utilizing any method known in the art. While shown here as a specific exploded structure, the structure should not be considered limiting but merely an example. For example, another structure may include the first material 102 being injection molded over second material 103 in a single shot process. Various manufacturing processes will be discussed in more detail below.

As shown in FIG. 1, the second material 103 may be sandwiched between an upper first material 102A and a lower first material 102B. Once fully assembled, the composite material may appear as a single, unitary element that includes each of the constituent materials, with the exterior showing only the first material 102 (although, in some embodiments, the pattern and/or weave of the second material 103 may shown through the exterior of the unitary element).

Figure 2A:
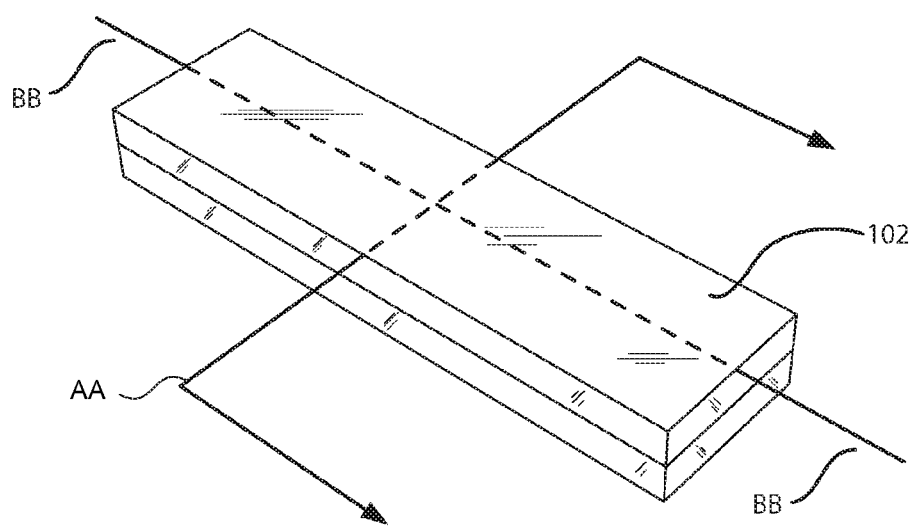
FIG. 2A illustrates a parallel projection view of an example of a composite material.
Figure 2B:
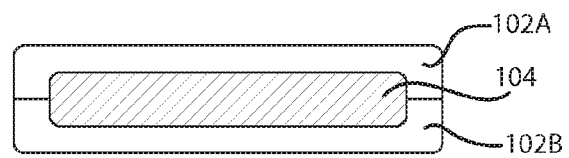
FIG. 2B illustrates a cross section side view of an example of a composite material.

As illustrated in FIG. 2A, the composite material 100 may be a continuous strip of material. FIG. 2A shows cross-sectional viewpoint lines AA and BB. FIG. 2B shows a generic example of a cross-sectional view of the composite material 100 as viewed from prospective AA. As shown in FIG. 2B, the composite material may include the first material 102A, first material 102B, and a core 104. The core 104 may be made from the second material 103 and may be located at the core of first material 102. Core 104 may be present regardless of whether the first material 102 includes multiple portions such as 102A and 102B or is a single contiguous exterior.

In accordance with various embodiments, the core 104 may be arranged in a variety of configurations. FIGS. 3A-3E illustrate various examples of the cross-section of the core 104 alone. These figures show the core 104 as it would run through the interior region of the first material 102.

The various layers of core 104, as illustrated in FIGS. 3A-3E, may be formed in any of a variety of configurations of the second material and may be utilized to form various core configurations. For example, a layer may be made up of a plurality of individual fibers laid out in a single direction or multiple directions, and may be woven or non-woven. Adjacent layers may be interconnected, may be in incidental contact, may be separated by a small layer of the first material, and so on. In one embodiment, as illustrated in FIG. 3A, a single layer 300 may form the core 104. FIG. 3A illustrates the same core 104 as shown in FIG. 2B.

In accordance with various embodiments, as illustrated in FIG. 3B, the core 104 may be formed from multiple layers. The arrangement may have a first layer 304 and a second layer 302. The second layer 302 may be narrower than the first layer 304. The second layer 302 may be a rib running along the top of layer 304 and may be positioned anywhere across the top of the first layer 304. For example, second layer 302 may be located at an edge of the first layer 304. In some embodiments and as also shown in FIG. 3B, a third layer 301 may also be included as part of the core 104. Although the second and third layers are shown as being separated from one another, they may be adjacent in certain embodiments.

By positioning the second and third layer 302/301 as stacked layers along the exterior edge of the first layer 304, a bolstering effect is applied to the composite material 100. This may cause the exterior edges of the core to increase in strength. This increase in strength along the exterior edges is accomplished without unnecessarily increasing the material in the center of the core 104. By avoiding material increase at the center of core 104 the drape ability of core 104 across its width may be preserved.

In accordance with various embodiments and as illustrated in FIG. 3C, the core 104 may include the components as described with regard to FIG. 3B but the core 104 may also include a lower layer 306 stacked below the first layer 304. This lower layer 306 may be wider, narrower, or the same width as first layer 304. Lower layer 306 may be positioned anywhere across the surface of the first layer 304. As shown in FIG. 3C, lower layer 306 may be the same width as first layer 304 and centered on first layer 304. By applying an additional layer below first layer 304, the drapeability of the composite material may be altered across the whole width. The addition of the lower layer 306 may also increase the strength along the length of the composite material. The addition of the lower layer 306 may also reduce flexibility along the length and width of the composite material.

In the embodiment illustrated in FIG. 3D, the core 104 may include the components as described with regard to FIG. 3B but may also include a fourth layer 303 stacked on top of the first layer 304. The three layers 301, 302, and 303 may be positions anywhere across the top of the first layer 304. Each of the three layers 301, 302, and 303 may be a different width than the others, or they may be all the same width as the others, or any combination of various widths. The three layers 301, 302, and 303 may be offset from either exterior edges of first layer 304. Likewise, the three layers 301, 302, and 303 may be in contact with one another or each of the three layers 301, 302, and 303 may be separated from one another (or certain layers may be in contact, while others are separated). As shown in FIG. 3D, the fourth layer 303 may be centered between the second layer 302 and the third layer 301 and offset from the exterior edges the first layer 304, although the position of this layer may vary in different embodiments.

By offsetting the three layers 301, 302, and 303 from the exterior edge of first layer 304, the drape of the edges of the composite structure may be altered in comparison to the embodiment shown in FIG. 3B. By adding an additional layer, such as fourth layer 303, the strength in elongation may be increased but the flexibility in elongation may be decreased. By utilizing only a narrow layer, the drapeability across the entire width of the composite material may be substantially unaltered but additional strength may be provided.

In the embodiment illustrated in FIG. 3E, the core 104 may include the components as described with regard to FIG. 3B but the core 104 may also include a transverse layer 308. As shown in FIG. 3E the core 104 may include the transverse layer 308 between the second layer 302 and the third layer 301. This transverse layer 308 may connect the second layer 302 and the third layer 301. Each of the layers as discussed herein may be any thickness. Each of the layers discussed herein may be different thicknesses from one another or each of the layers discussed herein may be the same thickness as one another. However, in at least one embodiment, the transverse layer 308 may be thinner than second layer 302 and third layer 301. The transverse layer 308 may connect the second layer 302 and the third layer 301 in such a way as to form a gap between the traverse layer 308 and the first layer 304. While FIG. 3E illustrates a cross-sectional view, in an isometric representation of the same structure, the first layer 304, second layer 302, transverse layer 308, and the third layer 301 would form a continuous channel along the length of the core 104. When assembling this embodiment of the core 104 with the first material, as shown for example, in FIGS. 1 and 2, the continuous channel along the length of core 104 under this embodiment may be empty. Meaning, the first material 102 may not fill the channel. Alternatively the first material 102 may fill the channel.

The transverse layer 308 forms a tensile bar between the second layer 302 and the third layer 301 internally within the composite material. This tensile bar may substantially modify drape\and also the strength across the width of and the length of the composite material.

Figure 4A:
FIG. 4A-D illustrates various examples of a fiber or fabric bias of material utilized in various composite materials viewed as a cross section along the length of the composite material from view BB indicated in FIG. 2A.

As indicated above, the specific layout of a second material along the length of the composite material may control the characteristics of the composite material. For example, the fibers that make up the second material may be laid out in a specific direction. In another example, a fabric that makes up the second material may be cut along a certain bias. FIGS. 4A-D illustrates various examples of a fiber or fabric bias in the second material. As shown in FIG. 4A, the core 104 may be made up the plurality of fibers indicated by the horizontal lines at the interior of the figure. These fibers may be parallel with the length of the composite material. These fibers may form core 104. By running the fibers along the length of the first material 102, the elongation of first material 102 is limited by the elongation of the core. That is, the composite material may stretch transversely (e.g., up and down with respect to the orientation of FIG. 4A but not longitudinally (e.g., left and right with respect to the orientation of FIG. 4A).

Figure 4B:
Figure 4C:
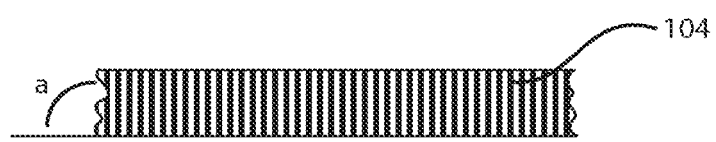

By changing the angle of the fibers relative to the length of the composite material 100, a compromise may be made between the natural elongation of the fibers that make up core 104 and the natural elongation of the first material 102. This is illustrated in FIG. 4B. Here the fibers are shown as angular lines, making up core 104. The fibers are set at an angle A relative to the length of the composite material. In accordance with various embodiments, angle A may be between 0 and 90 degrees. Specifically in one example, the angle A may be 45 degrees, as shown in FIG. 4B. In accordance with another embodiment, angle A may be 90 degrees as is illustrated in FIG. 4C. Here, the fibers are perpendicular to the length of the composite material 100. In this embodiment, the fibers may have very little effect on the elongation of the composite material 100. However, the flexibility and stretchability across the width of the composite material 100 may be limited to the flexibility of fibers that make up core 104

The structure of the core 104, as shown in the examples illustrated in FIGS. 3A-3E, may be combined with the embodiments discussed herein regarding direction of the various fibers. That is, each layer of the various examples illustrated FIGS. 3A-3E may be made up of fibers having any orientations discussed with respect to FIGS. 4A-4C. Furthermore, each layer may have a different orientation of fibers relative to the other layers. Alternatively, each layer may have the same orientation of fibers relative to the others.

In accordance with various embodiments, the fibers of the second material may be woven together into a fabric. The weave of the fabric may be any particular weave known to one of ordinary skill in the art. However, the weave may also be customized to further tune the characteristics of the composite material 100.

In one example, a fabric may have fibers running in two directions, such as perpendicular to one another. This fabric may be placed in the composite material with one set of fibers running parallel to the length of the material, with the other set of fibers running perpendicular to the material length. In such an embodiment, the composite material's flexibility in elongation and across its width would be limited by the associated sets of fibers.

Figure 4D:
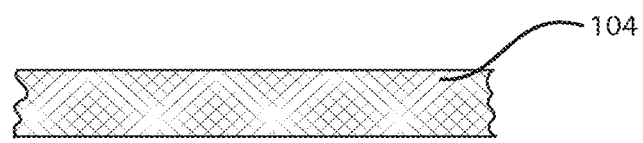

However, a fabric with fibers having a perpendicular weave may also be cut along the bias of the weave, e.g., at an angle to the direction of all the fibers in the fabric. The various fibers thus would not be parallel or perpendicular to either the length or width of the fabric. Rather, both directions of fibers may run at an angle to the length of the fabric, as illustrated in FIG. 4D.

Core 104 may be made up of a fabric having a perpendicular weave, with the bias of the weave positioned at an angle to the length of the composite material 100. In the configuration of the fibers, as shown in FIG. 4D, the fabric that makes up core 104 may have greater flexibility in elongation than a single constituent fiber would. Furthermore, the fabric may also improve the strength of the core 104. These characteristics may be provided to the composite material 100 by placing core 104, as shown in FIG. 4D into the first material 102. Thus, by manipulating the weave of a fabric that makes up the core 104, the characteristics of the composite material may be further adjusted to control the flexibility in elongation, the flexibility across the width of the composite material 100, the strength of the composite material, and the drape-ability of the composite material.

Furthermore, as discussed above with respect to the various orientations of individual fibers, each of the layers that make up core 104 may be made from various weaves of fabrics. In some embodiments, the sets of fibers running in a first direction may be formed from a first material and the set of fibers running in a second direction may be formed from a second material, or one or both sets may be formed from multiple materials. In other embodiments, multiple weaves of different fibers may be bonded together at different regions of the core to provide different structural characteristics to the composite material at different areas. Thus, the core characteristics may vary across a cross-section or in a region, and thus vary the characteristics (such as flexibility, drape, stretchability, minimum bend radius, and the like) of the composite material.

Figure 5A:
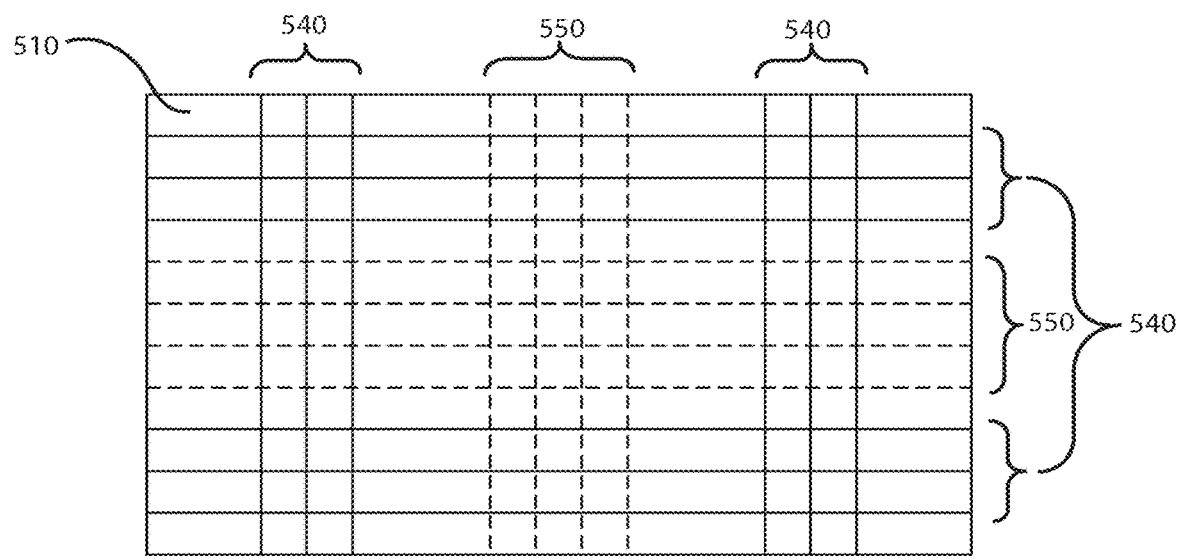

To elaborate and as illustrated in FIG. 5A-E, fabric or fibrous strand layout may include fibers with different characteristics. These various different fibers with various different characteristics may be oriented in the composite material individually. These various different fibers with various different characteristics may be woven into a fabric, which in turn may be included in the composite material 100. In accordance with various embodiments, as shown in FIG. 5A, a weave of fibers may consist of at least two different types of fibers. For example, fibers 540 may be a first type and fibers 550 may be a second type. The differences in the types of fibers may include material, size, continuity, or other difference. In one example, fibers 540 may be a KEVLAR fiber while fibers 550 may be a silicone fiber. This may provide different strength, different flexibilities, or different drape-abilities to different portions of the composite material and potentially preserve costs in other portions. In another example, fibers 540 may be a small diameter fiber while fibers 550 may be a large diameter fiber. Conversely, fibers 540 may be a large diameter fiber while fibers 550 may be a small diameter fiber. This may similarly provide different strength, different flexibilities, or different drape to different portions of the composite material and potentially preserve costs in other portions.

Figure 5B:
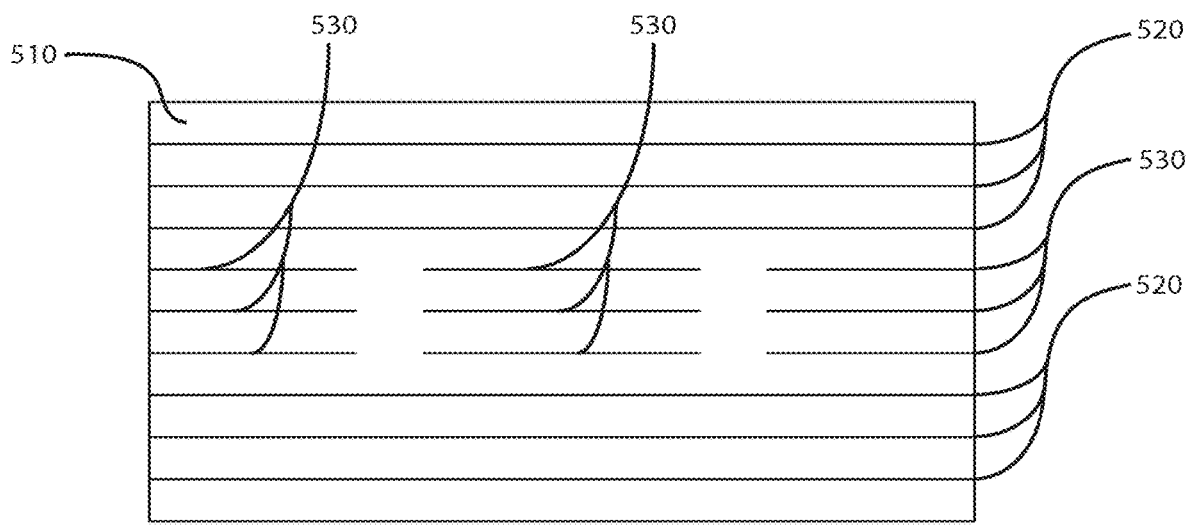

In accordance with various embodiments, as shown in FIG. 5B, some fibers 520 may be continuous while other fibers 530 may be discontinuous. For example, the discontinuous fiber 530 may run only short distances with regular breaks therebetween. Thus, the discontinuous fiber 530 is a series of axially-aligned fibers separated by gaps and that extend in the same direction to form a broken line.

Discontinuous fiber may create a substantially different flexibility in the composite material as compared to continuous fibers. This is because the flexibility of the composite material may be constrained by the flexibility of the continuous fiber, whereas the discontinuous fibers do not affect the natural flexibility of the suspension material 510 (e.g. silicone) in the regions between each of the breaks. It should be appreciated that the suspension material may be the same as the encapsulation material previously discussed. By staggering different lengths of broken fibers strategically, embodiments may be created that have ranges of flexibility, either overall or in localized areas. The flexibility of such embodiments may range between the flexibility of the suspension material 510 and the flexibility of the fiber.

Turning now to FIG. 5O, the composite material may have apertures 569 formed through the composite material. The apertures may pass through just one of the materials that make up the composite material. For example, the non-stretchable fiber/fabric core may be exposed by the aperture passing through the outer flexible portion of the composite material. As an alternative, the one or more layers of the outer flexible material may be present while the aperture extends through the non-stretchable fiber/fabric core.

In various embodiments, the outer flexible material may be a clear material (such as a clear silicone) and there may be no core at or near apertures 569. Thus a user may be able to see through the composite material. This may be useful for a band/cover on a heart rate monitor, blood pressure monitor, a light sensor, a watch, a camera or the like. The aperture may also extend all the way through the composite material, such as the holes in a belt.

In various embodiments, fibers 569 may encircle or border the outside of areas in which an aperture 569 is present (or simply the outside of the apertures themselves). The fibers 569 may reinforce and strengthen the apertures during use, such that a tab passing through hole does not tear or expand the hole.

Additionally, devices may be woven into the non-stretchable material or merely included within or near the non-stretchable material. The devices may then be overmolded by the flexible materials. In some embodiments, such devices may be placed at or near the aperture 569. Sample devices include a ridged plate, a magnet, a stiffener, a fastener, and the like. The aperture, device or other feature in the composite material may be any shape or size.

Turning now to FIG. 5O, in some embodiments the fibers 565A and 565B may not straight along the composite material (e.g., parallel to the length of the composite material). Instead, the fibers 565A and 565B form a wave-like pattern along the length or width of the composite material. The upper fibers 565A may be a mirror image of the lower fibers 565B in many embodiments, although in some embodiments the two patterns may differ. It should be appreciated that one or both sets of fibers have such a pattern in an embodiment using woven fibers for a core.

The waves may act much like an accordion and extend (e.g., flatten) under an expansive force, such that the flexibility of the composite material is not substantially limited by the natural flexibility of the fibers until the composite material has stretched to the point that the fibers 565A and 565B have straightened out. This concept is similarly represented in FIG. 5D, which shows the fibers 560 are laid out in a zigzag pattern in the suspension material 510. Again, while the presence of the of the fibers may limit the natural flexibility of the suspension material 510 somewhat but does not limit the natural flexibility of the suspension material 510 to the flexibility of the fiber until the composite material has stretched or flexed to the point where the fibers are straight (i.e. parallel to the direction which is flexed).

In accordance with various embodiments and as shown in FIG. 5E, a fabric or other core may extend out of the ends of the flexible material. As shown in FIG. 5E, the fabric 590 may extend out a distance "A" at one or more ends. While the non-stretchable material 590 may not be as flexible in elongation as the flexible material 510, the non-stretchable material 590 may have a smaller bend radius than the flexible material. As such, the extended portions "A" of the non-stretchable material portion may be useful to, for example, wrap around another device or merely connect to another device. It should be appreciated that the distance to which the non-stretchable material extends may vary between ends in some embodiments.

Figure 6A:
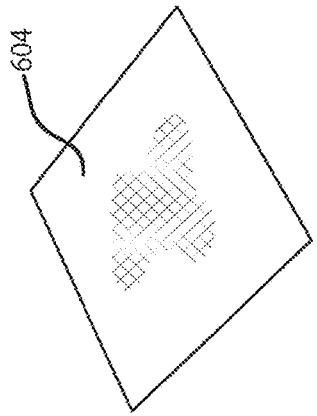
FIG. 6A-C illustrates an example of a hot pressing process for forming a composite material.
Figure 6B:
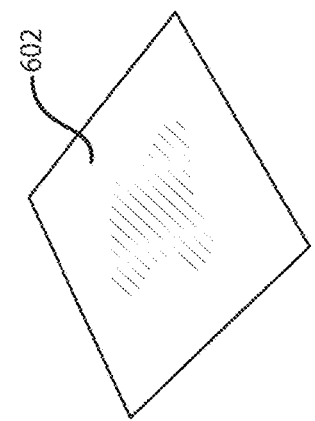
Figure 6C:
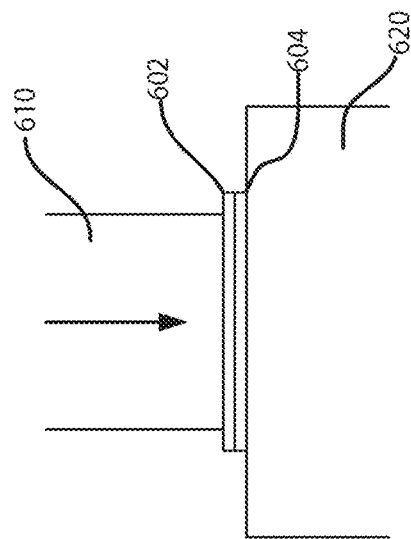

It may be appreciated that various systems may be used to form the structures discussed herein. FIGS. 6A-C illustrate an example of a hot pressing process for forming a composite material. As shown in FIGS. 6A and 6B, the hot press system may utilize sheets of a flexible material 602 and a sheet of a non-stretchable material 604, although in alternative embodiments more or fewer sheets of each type of material may be used.

The hot press system may also include a press 610 and a base 620 as shown in FIG. 6C. The press 610 may press down and against base 620. The sheets of flexible material 602 and sheet of non-stretchable material 604 may be placed between the press 610 and the base 620. The sheets may be heated before being placed in the press or the press 610 and base 620 may be operable to heat the sheets. The heat and pressure may cause the flexible material to flow around the non-stretchable material, thereby forming a composite material. The press system may also process multiple sheets to form a composite material. For example, in FIG. 6C the press is shown processing two sheets. However, the press could also press three or more sheets of material. For example, the non-stretchable material may be sandwiched between two sheets of flexible material. In this way the press system may form a composite material having a fully encapsulated core. The press may also have small forms that are able to cut the sheets of material and form small straps of the composite material during the heating and pressing cycle.

Figure 7A:
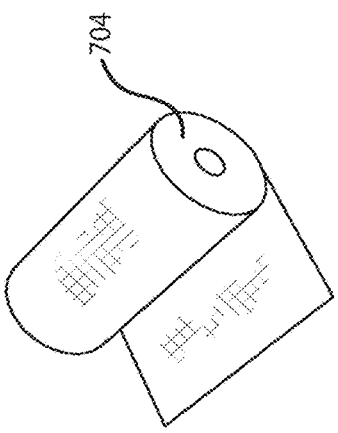
FIG. 7A-C illustrates an example of a hot rolling process for forming a composite material.
Figure 7B:
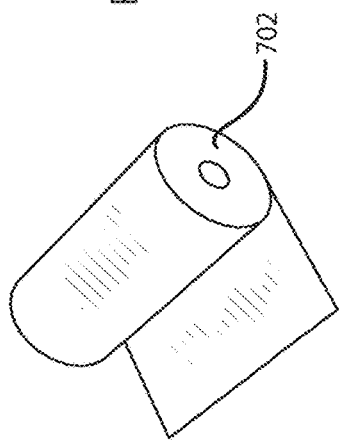
Figure 7C:
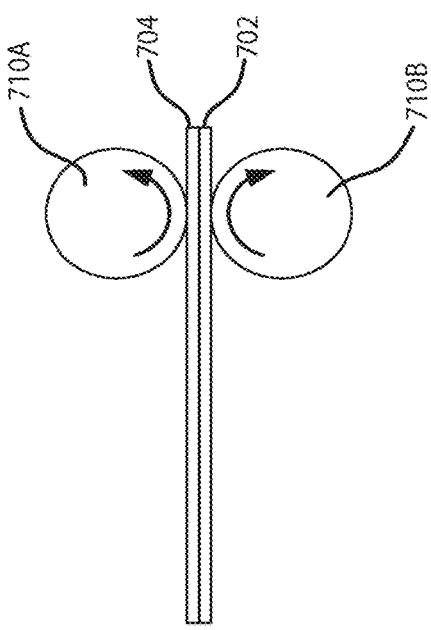

FIGS. 7A-C illustrate an example of a hot rolling process for forming a composite material. In accordance with various embodiments, as shown in FIGS. 7A and 7B the hot rolling system may utilize sheets of a flexible material 702 and sheets of a non-stretchable material 704. The hot rolling system may also include a roller 710A and roller 710B as shown in FIG. 7C. The rollers 710A 710B may press the material traveling between them together. The sheets of a flexible material 702 and sheets of a non-stretchable material 704 may be run between the rollers 710A/710B. The sheets may be heated before being placed in the rollers 710A/710B or after being placed between rollers 710A/710B. Likewise, the rollers 710A/710B may be operable to heat the sheets. The heat and pressure may cause the flexible material to flow around the non-stretchable material forming a composite material. As discussed above with respect to the pressing process of FIGS. 6A-6C, multiple sheets may be processed to form a composite material with a core, for example.

FIGS. 8A-G illustrate an example of a schematic of a compression molding system for forming a composite material. In accordance with various embodiments, as shown in FIG. 8A the compression molding system may utilize sheets of a flexible material 802 and sheets of a non-stretchable material 804. A sheet punch may cut slots 806 form the material sheets in the direction of arrow A. The portions of material removed from the slots 806 may form strips of flexible material 802 and/or strips of non-stretchable material 804. In various embodiments and as shown in FIG. 8A, the flexible material 802 and the non-stretchable material 804 may be stacked prior to punching. Thus, the two materials' strips 802/804 may be formed at the same time.

As shown in FIG. 8B the compression mold may utilize lower form 820. The non-stretchable material 804 may be placed in this lower mold with the flexible material 802A placed on top of the non-stretchable material 804. As shown in FIG. 8C, an upper form 810 may then be placed over top the lower form, the non-stretchable material 804, and the flexible material 802A. The upper form 810 and the lower form 820 may be operable to heat the entire system and/or place the non-stretchable material 804 and the flexible material 802A under pressure. This heat and pressure may cause the flexible material 802A to flow around or through the non-stretchable material 804, thus forming a partial composite material. The system may then be utilized to apply another layer of flexible material 802 to the opposite side of the half composite material shown in FIG. 8D. In alternative embodiments, the compression mold may mold both upper and lower flexible materials to the non-stretchable material used as a core, thus forming the entire composite material in a single molding operation.

Turning now to FIG. 8E, the compression mold may utilize lower form 820. The flexible material 802B may be placed in the lower form 820. The non-stretchable material 804 may be placed between the flexible material 802B and the flexible material 802A. As such two outer flexible materials and a core non-stretchable material may be place in the lower form 820. The upper form 810, as shown in FIG. 8C, may then be seated on to the lower form 820. Similar to the above, the upper form 810 and the lower form 820 may be operable to heat the entire system. This heat and pressure may cause the flexible material 802A and 802B flow around or through the non-stretchable material 804. This may form a composite material as shown by the cross section of the composite material in FIG. 8F. The non-stretchable material 804 may form the core with the flexible materials 802A and 802 B fully encapsulating the non-stretchable material 804. An example of the composite material is shown in FIG. 8G. However, it should be noted that after the compression molding, the separation lines between the flexible materials 802A/B may not be visible but are visible in FIG. 8G merely to illustrate the joining of multiple portions of flexible material in this example.

Figure 9:
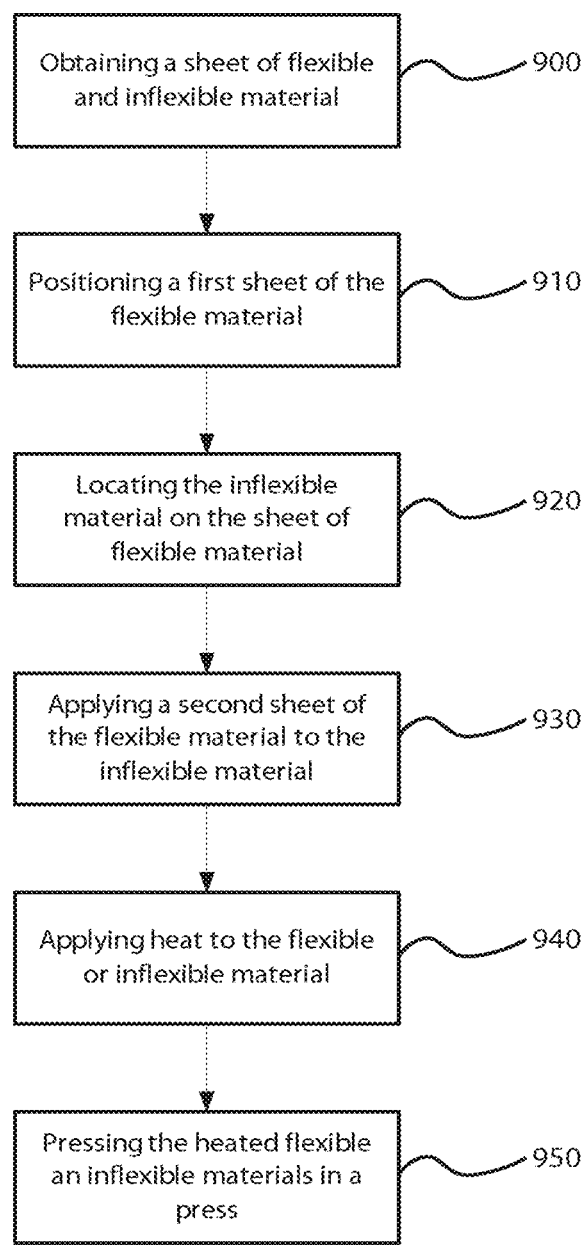
FIG. 9 illustrates a flow chart depicting a method for hot pressing a composite material.

As discussed above, a composite material may have particular features (such as an exterior formed from first material with a structured core formed from a second material). FIG. 9 generally shows an example method of forming the composite material by hot pressing the first material around the second material. The first and second material may be obtained as shown in operation 900. As indicated above the first material may be a silicone rubber. The second material may be formed as a structured core. The structured core may include one or more layers formed from strands of material or it may include one or more layers of a woven fabric. Non-stretchable material may include all those materials consistent with the discussion above (e.g. glass, cotton, nylon, KEVLAR, etc.)

In operation 910, the first material may be positioned to begin the process of combining the materials. In operation 920, the non-stretchable material may be located on the flexible material. The sheet of non-stretchable material may be smaller than the sheet of flexible material. This may allow for the non-stretchable material to be entirely encompassed within the flexible material during the combination of the materials.

In operation 930, a second sheet of the flexible material may be applied to the non-stretchable material. The second sheet of flexible material may be applied to the non-stretchable material. The non-stretchable material may be sandwiched between the flexible and the non-stretchable material. The application of the second sheet of flexible material may fully encapsulate the non-stretchable material within the flexible material.

In operation 940, heat may be applied to the first sheet or the second sheet. The application of the heat may melt or make the flexible material sufficiently pliable such that it may be formed around or flow through the non-stretchable fibers or fabric. In operation 950, the first sheet and second sheet, with the non-stretchable material sandwiched therein, may be pressed together utilizing a press. The pressure from the press may further or ultimately cause the flexible material to encapsulate or flow around the non-stretchable fibers/fabric. This may result in the combining of the flexible material and the non-stretchable material into a composite strip of material with the flexible material as the exterior and the non-stretchable material as the core.

Figure 10:
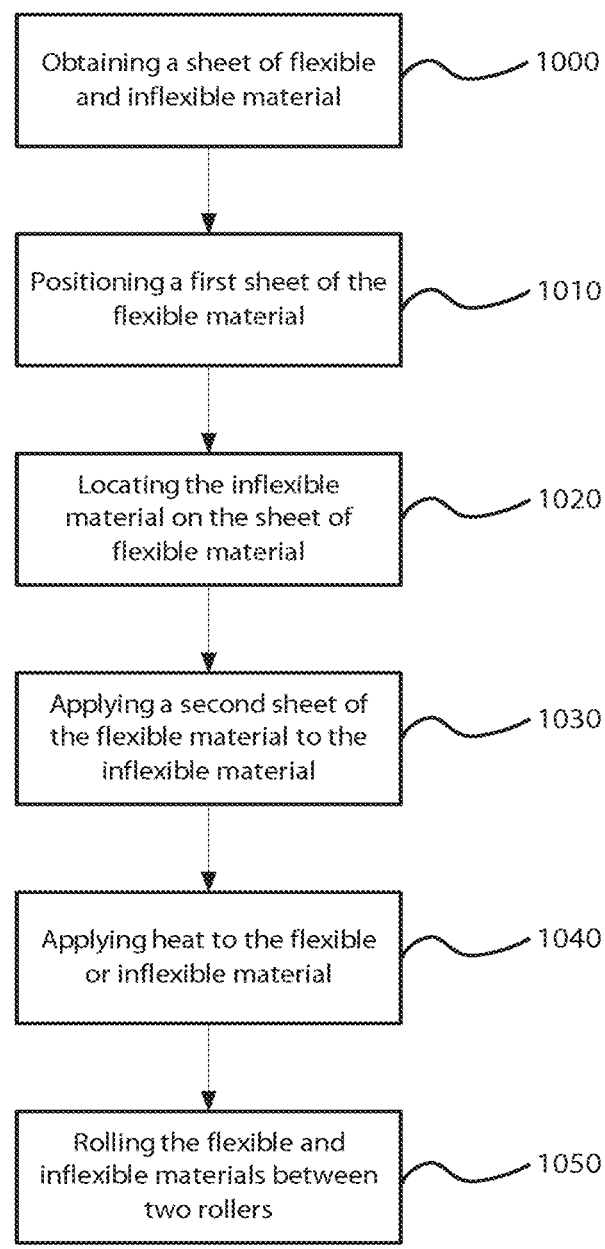
FIG. 10 illustrates a flow chart depicting a method for hot rolling a composite material.

FIG. 10 generally shows an example method of forming the composite material by hot rolling the first material around the second material. The hot rolling method of forming the composite material is much like the hot pressing with the exception of utilizing rollers to apply the pressure as opposed to the press. The first and second material may be obtained as shown in operation 1000. As indicated above the first material may be a silicone rubber. The second material may be formed as a structured core. The structured core may include one or more layers formed from strands of material or it may include one or more layers of a woven fabric. Non-stretchable material may include all those materials consistent with the discussion above.

In operation 1010, the first layer of material may be positioned to begin the process of combining the materials. In operation 1020, the non-stretchable material may be located on the layer of flexible material. Again, the layer of non-stretchable material may be smaller than the layer of flexible material. This may allow for the non-stretchable material to be entirely encompassed within the flexible material during the combination of the materials.

In operation 1030, a second layer of the flexible material may be applied to the non-stretchable material. Applying the second layer of flexible material to the non-stretchable material, the non-stretchable material may be sandwiched between the flexible and the non-stretchable material. The application of the second layer of flexible material may fully encapsulate the non-stretchable material within the flexible material.

In operation 1040, heat may be applied to the first layer or the second layer. The application of the heat may melt or make the flexible material sufficiently pliable such that it may be formed around or flow through the non-stretchable fibers or fabric. In operation 1050, the first layer and second layer, with the non-stretchable material sandwiched therein, may be rolled together between two rollers. The pressure from the rollers may further or ultimately cause the flexible material to encapsulate or flow around the non-stretchable fibers/fabric. This may result in the combining of the flexible material and the non-stretchable material into a composite strip of material with the flexible material as the exterior and the non-stretchable material as the core.

Figure 11:
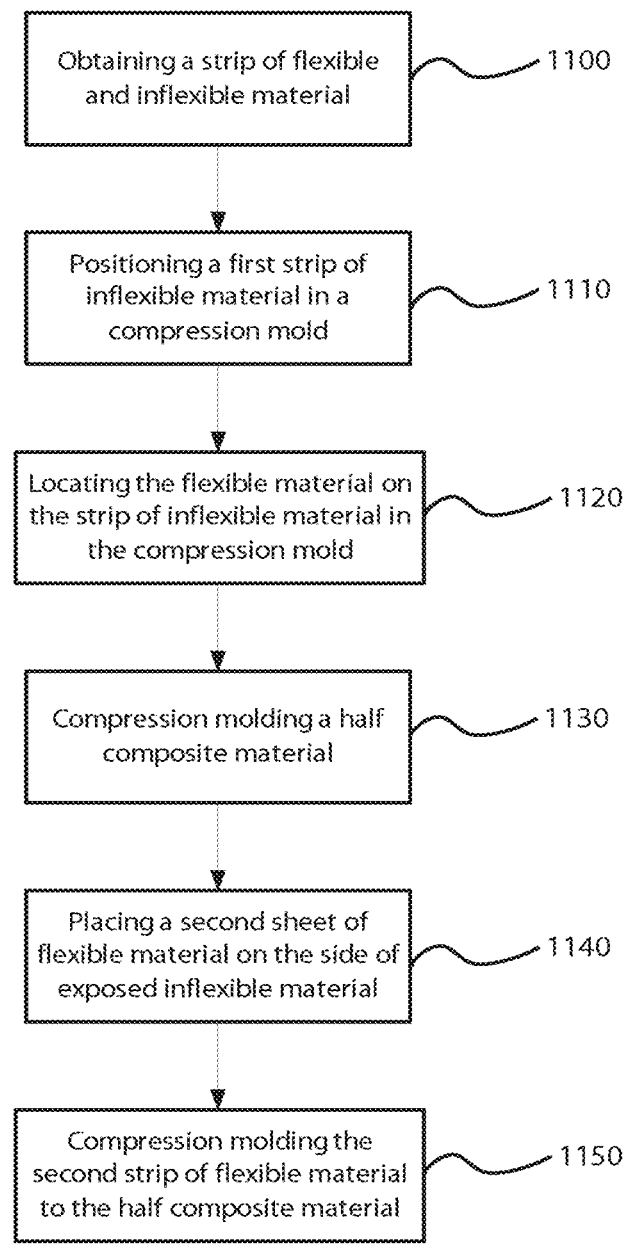
FIG. 11 illustrates a flow chart depicting a method of a compression molding for forming a composite material.

FIG. 11 generally shows an example method of forming the composite material by compression molding the first material around the second material. The first and second material may be obtained as shown in operation 1100. As indicated above the first material may be a silicone rubber. The second material may be formed as a structured core. The structured core may include one or more layers formed from strands of material or it may include one or more layers of a woven fabric. Non-stretchable material may include all those materials consistent with the discussion above. Obtaining the flexible and non-stretchable material may be accomplished by punching strips out of a flexible sheet of material In operation 1110, the second strip of material, the non-stretchable material, may be positioned in a compression mold to begin the process of combining the materials. In operation 1020, the first strip of material, the flexible material may be located on the strip of flexible material. The relative quantity of material may be such that the non-stretchable material is able to be entirely encompassed within the flexible material during the combination of the materials.

In operation 1130, a half composite material may be compression molded. A top mold half may be applied above the flexible material and non-stretchable material, compressing the two materials in the mold. Heat may also be added to the process. Through the heat and pressure, the flexible material may form around and through the non-stretchable material. By compression molding the flexible material to just one side of the non-stretchable material, a composite material may be formed. However, it may be noted that in other embodiments, the non-stretchable material may be sandwiched between two flexible strips of material. The entire stack may then be compression molded.

In operation 1140, a second strip of flexible material may be placed on the half composite material. The strip of flexible material may be applied to the side of the half composite material with exposed non-stretchable material. In operation 1150, the second strip of flexible material may be compression molded to the half composite material. Again, heat may be added to the process. Because of the heat and pressure, the flexible material may adhere to and form around and through the non-stretchable material and the flexible material already adhered to the non-stretchable material.

As used throughout this document and with respect to each of the embodiments, aspects, examples, lists and various descriptions of the subject matter contained herein, the word "or" is intended to be interpreted in its inclusive form (e.g. and/or) not in its exclusive form (e.g. only one of) unless explicitly modified to indicate only one item in a list is intended (e.g. only one of A, B, or C). For example, the phrase A, B, or C is intended to include any combination of the elements. The phrase can mean only A. The phrase can mean only B. The phrase can mean only C. The phrase can mean A and B. The phrase can mean A and C. The phrase can mean B and C. The phrase can mean A and B and C. This concept extends to any length of list (e.g. 1, 2, 3 . . . n) used herein.

Although the foregoing discussion has presented specific embodiments, the foregoing merely illustrates the principles of the invention. Persons skilled in the art will recognize that changes may be made in form and detail without departing from the spirit and scope of the disclosure as various modifications and alterations to the described embodiments will be apparent to those skilled in the art, in view of the teachings herein. For example, the processing steps may be performed in another order, or in different combinations. It will thus be appreciated that those having skill in the art will be able to devise numerous systems, arrangements and methods which, although not explicitly shown or described herein, embody the principles of the disclosure and are thus within the spirit and scope of the present invention. From the above description and drawings, it will be understood by those of ordinary skill in the art that the particular embodiments shown and described are for purposes of illustration only, and references to details of particular embodiments are not intended to limit the scope of the present invention, as defined by the appended claims.

We claim:

1. A band for a watch, the band comprising:
   a first flexible, bendable, elongatable material forming apertures extending through a thickness of the band;
   a second flexible material that resists elongation in at least one direction, wherein the second material is encapsulated by the first material, the second material forming:
   first fibers extending along a length of the band past the apertures, wherein an opposing pair of the first fibers are a first distance away from each other across one of the apertures and a second distance, smaller than the first distance, away from each other at a location between an adjacent pair of the apertures; and
   second fibers, wherein each of the second fibers encircles a corresponding one of the apertures; and
   a tab for passing through one of the apertures during use of the band.

2. The band of claim 1, wherein the second material is one of glass, nylon, Poly-paraphenylene terephthalamide, or cotton fiber strands.

3. The band of claim 1, wherein the first material is silicone.

4. The band of claim 1, wherein the first fibers extend along the length of the band to each of opposing ends of the band, thereby limiting the elongation of the length of the band to the elongation of the second material.

5. The band of claim 1, wherein the first fibers are formed from a plurality of different fiber materials.

6. The band of claim 1, wherein the first fibers limit an elongation of the band in at least one direction.

7. The band of claim 1, wherein at least two of the first fibers define a gap, the at least two of the first fibers axially aligned with one another to form a broken line.

8. The band of claim 1, further comprising third fibers, wherein each of the third fibers encircles a corresponding one of the apertures and second fibers.

9. The band of claim 1, further comprising a device within one of the apertures and covered by the first flexible, bendable, elongatable material.

10. A band for a watch, the band comprising:
    a cover comprising a first flexible, bendable, elongatable material;
    first fibers extending along a length of the band, wherein a first set of the first fibers extend along a first axis and are axially separated from each other by at least one first gap, and a second set of the first fibers extend along a second axis and are axially separated from each other by a second gap, wherein the first gap is aligned with the second gap such that adjacent pairs of the first fibers that are parallel with each other have coextensive lengths;
    second fibers extending in parallel with the first fibers and continuously past each of the first fibers on a first side of the first fibers; and
    third fibers extending in parallel with the first fibers and continuously past each of the first fibers on a second side of the first fibers opposite the first side, wherein the first fibers, the second fibers, and the third fibers are encapsulated by the cover.

11. The band of claim 10, wherein the second fibers are oriented parallel to the length of the band, thereby limiting the elongation of the length of the band to the elongation of the second fibers.

12. The band of claim 10, wherein the first fibers are formed from a plurality of different fiber materials.

13. The band of claim 10, wherein the cover comprises a suspension material filling the first gap and the second gap.

14. The band of claim 13, wherein the suspension material comprises silicone.

15. The band of claim 10, wherein the band is more flexible at each of the first gap and the second gap than at the first fibers.

* * * * *